United States Patent [19]

Buysch et al.

[11] Patent Number: 4,587,347

[45] Date of Patent: May 6, 1986

[54] N-PHENYL-N'-VINYLETHYLENEUREAS

[75] Inventors: Hans-Josef Buysch, Krefeld; Reinhold Klipper, Cologne; Peter M. Lange, Leverkusen; Peter Mues, Krefeld, all of Fed. Rep. of Germany

[73] Assignee: Bayer Aktiengesellschaft, Leverkusen, Fed. Rep. of Germany

[21] Appl. No.: 628,175

[22] Filed: Jul. 6, 1984

[30] Foreign Application Priority Data

Jul. 9, 1983 [DE] Fed. Rep. of Germany ....... 3324903

[51] Int. Cl.$^4$ ........................................... C07D 233/34
[52] U.S. Cl. .................................. 548/317; 548/320; 548/322
[58] Field of Search ....................... 548/320, 322, 317

[56] References Cited

U.S. PATENT DOCUMENTS

| 2,880,208 | 3/1959 | Yost | 548/317 |
|---|---|---|---|
| 4,026,934 | 5/1977 | Daum et al. | 424/245 |
| 4,144,344 | 3/1979 | Eichenberger et al. | 544/296 |

FOREIGN PATENT DOCUMENTS

| 2035364 | 2/1971 | Fed. Rep. of Germany | 548/320 |
|---|---|---|---|
| 364828 | 11/1981 | Fed. Rep. of Germany | 424/273 R |

OTHER PUBLICATIONS

Shenoy et al., "2-Imidazolidinones (Ethylene Ureas)—A Review", Amer. Dye Report, 10, pp. 352–369 (1968).

Primary Examiner—Richard A. Schwartz
Assistant Examiner—Kurt G. Briscoe
Attorney, Agent, or Firm—Sprung Horn Kramer & Woods

[57] ABSTRACT

Substituted ethyleneureas are prepared by reacting appropriate β-hydroxyethylureas with alkyl carbonates in the presence of catalysts at an elevated temperature.

Substituted ethyleneureas are used, inter alia, as polymerization and copolymerization components for the preparation of plastics, coatings, surface finishes and ion exchangers.

1 Claim, No Drawings

N-PHENYL-N'-VINYLETHYLENEUREAS

The invention relates to a process for the preparation of substituted ethyleneureas and to new N-vinylethyleneureas.

The preparation of disubstituted ethyleneureas by addition of epoxides onto carbodiimides is disclosed in, for example, Chem. Ber. 94,3287 (1961). The disadvantages of this process are the high reaction temperatures necessary (200° C.), the long reaction times (3 to 10 hours) and the costly starting products. In addition, the preparation of substituted ethyleneureas by reacting substituted ethylenediamines with phosgene or carbonic acid derivatives to give carbamic esters and their thermal cyclization has been disclosed (J. Org. Chem. 26, 4051 (1961)). This process has the disadvantage that the ethylenediamines to be employed are frequently difficult to prepare and thus are very costly. According to German Offenlegungsschrift No. 2,230,076 and German Offenlegungsschrift No. 2,035,364, substituted ethyleneureas can be prepared by cyclisation of N-β-chloroethylureas with elimination of hydrogen halide. The disadvantages of this process are the use of highly corrosive thionyl chloride for the preparation of the N-β-chloroethylureas from the corresponding N-β-hydroxyethylureas, and the formation of hydrogen chloride or sodium chloride on cyclization. A similar cyclization process for the preparation of substituted ethyleneureas is disclosed in Helv. Chem. Acta 49, 2400 (1966) and in Bull. Chem. Soc. Japan 39, 708 (1966). In the cyclization processes described in these articles, the sulphate and phosphite groups are the respective leaving groups. The disadvantages of this process are the unsatisfactory yields which result, inter alia, from the introduction of the leaving group, and the disposal of the waste products produced on cyclization. In addition, the preparation of N-vinylethyleneurea, N,N'-divinylethyleneurea and of N-ethyl-N'-vinylethyleneurea has been disclosed (compare U.S. Pat. No. 2,541,152 and J. Macromol. Sci. Chem. A9, 1085 (1975)). The processes for the preparation of vinylethyleneureas have in common the fact that they start from previously supplied ethyleneurea, either the potassium salt of the urea being reacted with acetylene under pressure, or the vinyl compound being obtained in a multistep synthesis via a Hofmann degradation. The disadvantages of these processes are, on the one hand, that extensive safety measures and technically complicated equipment are necessary for working with acetylene under pressure and, on the other hand, that synthesis via the Hofmann degradation is laborious and involves the use of costly starting materials.

A process has now been found for the preparation of substituted ethyleneureas of the formula (I)

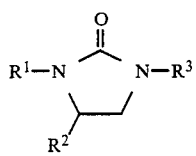

in which
$R^1$ represents a phenyl radical which is optionally monosubstituted or polysubstituted by chlorine, bromine, a nitro group, a trifluoromethyl group, an alkoxy group having 1 to 4 carbon atoms or a carbalkoxy group having 1 to 4 carbon atoms,
$R^2$ denotes hydrogen or methyl, and
$R^3$ represents a phenyl radical which is optionally monosubstituted or polysubstituted by chlorine, bromine, a nitro group, a trifluoromethyl group, an alkoxy group having 1 to 4 carbon atoms or a carbalkoxy group having 1 to 4 carbon atoms, an alkyl radical having 1 to 4 carbon atoms, or

$R^4$ representing $C_1$–$C_4$-alkyl, or —CH=CHR$^2$, where $R^2$ has the abovementioned meaning,
which process is characterised in that β-hydroxyethylureas of the formula (II)

in which
$R^1$ and $R^2$ have the abovementioned meaning, and
$R^5$ represents a phenyl radical which is optionally monosubstituted or polysubstituted by chlorine, bromine, a nitro group, a trifluoromethyl group, an alkoxy group having 1 to 4 carbon atoms or a carbalkoxy group having 1 to 4 carbon atoms, an alkyl radical having 1 to 4 carbon atoms, or —CH$_2$CHR$^2$OH, where $R^2$ has the abovementioned meaning,
are reacted, in the presence of catalysts, at an elevated temperature, with alkyl carbonates of the formula (III)

in which $R^6$ and $R^7$ are identical or different and represent an alkyl radical having 1 to 4 carbon atoms.

Alkyl radicals in the formulae (I) to (III) having 1 to 4, preferably 1 or 2, carbon atoms which may be mentioned are: the methyl, ethyl, n-propyl, isopropyl, n-butyl, isobutyl and tert.-butyl radicals, preferably the methyl and ethyl radicals.

. Alkoxy groups in the formulae (I) and (II) having 1 to 4, preferably 1 or 2, carbon atoms which may be mentioned are: the methoxy, ethoxy, n-propyloxy, isopropyloxy, n-butyloxy, isobutyloxy and tert.-butyloxy radicals, preferably the methoxy and ethoxy radicals, and carbalkoxy groups in the formula (I) and (II) having 1 to 4, preferably 1 or 2, carbon atoms: methoxycarbonyl, ethoxycarbonyl, n-propyloxycarbonyl, isopropyloxycarbonyl, n-butyloxycarbonyl, isobutyloxycarbonyl and tert-butyloxycarbonyl, preferably methoxycarbonyl and ethoxycarbonyl.

For example, the following can be employed as compounds of the formula (II) in the process according to the invention:
N-phenyl-N'-2-hydroxyethyl-N'-methylurea, N-(3,4-dichlorophenyl)-N'-2-hydroxyethyl-N'-methylurea, N-phenyl-N'-2-hydroxyethyl-N'-phenylurea, N-phenyl-N',N'-bis(2-hydroxyethyl)urea, N-(3,4-dichlorophenyl)-N',N'-bis(2-hydroxyethyl)urea, N-(4-nitrophenyl)-N',N'-bis(2-hydroxyethyl)urea, N-(4-ethoxyphenyl)-N',N'-bis(2-hydroxyethyl)urea or N-(4-methylphenyl)-N',N'-bis(2-hydroxyethyl)urea.

The abovementioned β-hydroxyethylureas can be obtained in a straightforward manner by addition of amines of the formula $HNR^5CH_2CHR^2OH$, with the abovementioned meaning for $R^2$ and $R^5$, onto isocyanates of the formula $R^1NCO$, with the abovementioned meaning for $R^1$, in the presence of an inert organic solvent, such as methylene chloride, ethylene chloride, chlorobenzene and/or o-dichlorobenzene, or directly in the presence of a carbonic ester to be employed for the subsequent transesterification, such as dimethyl carbonate or diethyl carbonate. The β-hydroxyethylureas of the formula (II) can likewise be obtained by aminolysis of appropriate urethanes with amines of the formula $HNR^5CH_2CHR^2OH$, with the above-mentioned meaning for $R^2$ and $R^5$. Both the addition of the amines onto the isocyanates and the aminolysis of urethanes are carried out under the reaction conditions customary for this purpose (compare "Methoden zur Herstellung und Umwandlung von substuierten Harnstoffen, Semicarbaziden, Isoharnstoffen" (Methods for the preparation and transformation of substituted ureas, semicarbazides and isoureas), Houben-Weyl, 4th edition, volume 8, page 149 et seq.).

The following may be mentioned as examples of isocyanates of the formula $R^1NCO$:
isocyanatobenzene, 1-chloro-3-isocyanatobenzene, 1-chloro4-isocyanatobenzene, 1,2-dichloro-4-isocyanatobenzene, 1-isocyanato-2-nitrobenzene, 1-isocyanato-4-nitrobenzene, 1-isocyanato-2-methylbenzene, 1-isocyanato-4-methylbenzene, 2-chloro-4-isocyanato-1-trifluoromethylbenzene, 1-ethoxy-4-isocyanatobenzene and 1-carboethoxy-4-isocyanatobenzene; and as amines of the formula $HNR^5CH_2CHR^2OH$:
2-methylaminoethanol, 2-ethylaminoethanol, N-(2-hydroxyethyl)aniline, 1-methylamino-2-propanol, bis(2-hydroxyethyl)amine and bis(2-hydroxypropyl)amine.

Using the process according to the invention, the reaction of the β-hydroxyethylureas of the general formula (II) with carbonic esters of the general formula (III) is carried out in the presence of catalysts at temperatures in the range from about 100° to 270° C., preferably at 110° to 160° C.

The alkyl carbonates of the formula (III) which may be mentioned are those having alkyl radicals containing 1 to 4 C atoms, preferably 1 or 2 C atoms, such as dimethyl, diethyl, di-n-propyl, diisopropyl, di-n-butyl, diisobutyl and di-tert.-butyl carbonate, preferably dimethyl carbonate and diethyl carbonate.

Relative to the β-hydroxyethylurea of the formula (II) employed, the alkyl carbonate can be employed in amounts which are below, above or equal to equimolar amounts. The molar ratio of the β-hydroxyethylurea to be employed to the alkyl carbonate to be employed which is preferably selected is about 1:1 to 1:20, particularly preferably 1:4 to 1:8.

The reaction of the β-hydroxyethylureas with the alkyl carbonate can be carried out with or without an inert organic solvent. Examples of suitable inert organic solvents are: xylenes, halogenated hydrocarbons, such as o-dichlorobenzene, and ethers, such as anisole.

Catalysts, which are employed in amounts of about 0.001 to 5% by weight, preferably 0.01 to 1% by weight, relative to the amount of compound of the formula (II) employed, and which may be mentioned are: the compounds of lithium, sodium, potassium, rubidium, caesium, magnesium, calcium, zinc, strontium, cadmium, barium, thallium, titanium, tin and/or lead, preferably the compounds of alkali metals and/or alkaline earth metals. In general, the hydroxides, alcoholates or salts having an alkaline reaction, such as the carbonates or the carboxylates, of the metals mentioned are employed. The carbonates, carboxylates, alcoholates and/or hydroxides of sodium and/or potassium, such as sodium hydroxide, sodium ethanolate and/or potassium carbonate, are preferably employed in the process according to the invention.

Using the process according to the invention, the substituted ethyleneureas of the formula (I) are preferably isolated by distillation under reduced pressure (about 0.01 to 100 mbar).

The invention also relates to new vinylethyleneureas of the formula (IV)

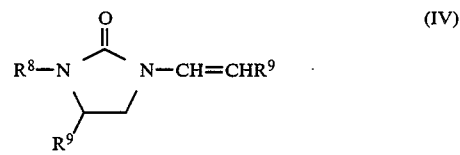

(IV)

in which $R^8$ represents a phenyl radical which is optionally monosubstituted or polysubstituted by chlorine, bromine, a nitro group, a trifluoromethyl group, an alkoxy group having 1 to 4 carbon atoms or a carbalkoxy group having 1 to 4 carbon atoms, and $R^9$ denotes hydrogen or methyl.

New N-vinylethyleneureas which can be obtained by the process according to the invention and which may be mentioned are: N-phenyl-N'-vinylethyleneurea, N-(3,4-dichlorophenyl)-N'-vinylethyleneurea, N-(4-nitrophenyl)-N'-vinylethyleneurea, N-(4-ethoxyphenyl)-N'-vinylethyleneurea and N-(4-methylphenyl)-N'-vinylethyleneurea, preferably N-phenyl-N'-vinylethyleneurea and N-(3,4-dichlorophenyl)-N'-vinylethyleneurea.

The new N-vinylethyleneureas are obtained using the process according to the invention by starting from, for example, β-hydroxyethylureas of the formula (II) (with $R^5=-CH_2CHR^2OH$) and reacting them with alkyl carbonates of the formula (III) in the manner described.

In this process, it is possible only under certain conditions to isolate the initially formed ethyleneureas of the formula (V)

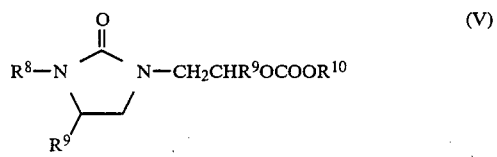

(V)

in which $R^8$ and $R^9$ have the previously mentioned meaning (formula IV) and $R^{10}$ represents $C_1$-$C_4$-alkyl.

The ethyleneureas of the formula (V) are likewise new.

The isolation of the ethyleneureas of the formula (V) is carried out in an advantageous manner by removing the catalysts from the reaction mixture by, for example, extraction with water or dilute acids, such as hydrochloric acid, sulphuric acid or acetic acid, or by an adsorption process, such as adsorption on active charcoal or kieselguhr. Moreover, it is possible to employ ion exchangers to remove the catalysts. Examples of this type of ion exchangers are acid-activated fuller's earths or exchanger resins based on sulphonated styrene/divinylbenzene copolymers.

Isolation of the ethyleneureas of the formula (V) in the presence of the transesterification catalyst can also be achieved if the reaction mixture in which they are contained is not subjected to temperatures any higher than 160° C., and preferably not to temperatures any higher than 140° C., and when it is not mixed with solvents (for example for crystallization purposes) which are capable of reacting with organic carbonates, such as, for example alcohols, such as ethanol or methanol.

It is easy to obtain the N-vinylethyleneureas of the formula (IV) from the ethyleneureas of the formula (V) without removing the catalyst present in the reaction mixture, by heating to temperatures of about 160° to 270° C., preferably 180° to 250° C., and then distilling under reduced pressure at about 0.01 to 100, preferably 0.01 to 20 mbar.

For further purification of the product thereby obtained, it is possible to recrystallize from a suitable solvent, such as toluene, ethyl acetate and/or ethanol.

The alcohol produced in the reaction, for example methanol or ethanol, is advantageously condensed in a cold trap charged with dry ice, while the carbon dioxide is trapped either in a trap cooled with liquid nitrogen or in a suitable liquid, such as ethanolamine or ethylenediamine, with the formation of a carbamate.

Ethyleneureas of the formula (IV) are valuable precursors. They are used, inter alia, as polymerization and copolymerization components for the preparation of plastics, coatings, surface finishes and ion exchangers. For example, ion exchangers can be preared by reacting vinylethyleneureas of the general formula (IV) with divinylethyleneurea, divinylbenzene, diethylene glycol divinyl ether, butanediol divinyl ether, 2,3-dimethyl-1,5-hexadiene, butanediol diacrylate, 1,5-hexadiene-3,4-diol carbonate and/or 1,5-hexadiene-3,4-diol diacetate as crosslinking agents, with the addition of polymerization initiators, at an elevated temperature and hydrolyzing the crosslinked polymers formed in the presence of bases or acids at an elevated temperature. The following procedure can be followed:

(a) 37.1 g of N-phenyl-N'-vinylethyleneurea ((IV) in which $R^8=C_6H_5$ and $R^9=H$), 5 g of divinylethyleneurea and 0.2 g of azodiisobutyronitrile are introduced in succession into 200 ml of toluene. The mixture is stirred for 10 hours at 60° C., 5 hours at 70° C. and 5 hours at 90° C. A polymer is produced which is extracted for 24 hours with acetone. 32.3 g of a crosslinked polymer corresponding to 76.7% by weight—based on the quantity of monomer employed—remain.

(b) 25 g of N-phenyl-N'-vinylethyleneurea, 5 g of divinylbenzene —containing 63% of isomers of divinylbenzene—and 0.15 g of 75% dibenzoyl peroxide are introduced into 200 ml of toluene. The mixture is stirred for 10 hours at 70° C. and 5 hours at 85%. 15.6 g of a polymer are produced.

Instead of the divinyl compounds mentioned in (a) and (b) it is also possible to use the compounds already mentioned above as crosslinking agents.

In all of the reactions crosslinked polymers are formed, the hydrolysis of which, according to (c) or (d) results in products having ion-exchanging properties:

(c) 20.3 g of the exctracted polymer from test (a) are introduced into 700 g of 10% by weight sodium hydroxide solution and stirred at 95° C. for 12 hours. 17.7 g of a polymer having ion-exchanging properties are produced. It exhibits a total basic capacity of 0.9 milliequivalents per gram.

(d) 32.2 g of the extracted polymer from test (a) are introduced into 600 g of 10% by weight $H_2SO_4$ solution and stirred at 95° C. for 6.5 hours. 26.8 g of a polymer having ion-exchanging properties are produced. It exhibits a total basic capacity of 1.1 milliequivalent per gram.

The examples which follow are intended to make the process according to the invention clear.

EXAMPLE 1

N-Methyl-N'-phenyl-ethyleneurea(-imidazolidinone)

179 g (0.92 mol) of N-2-hydroxyethyl-N-methyl-N'-phenylurea, 472 g (4 mol) of diethyl carbonate and 0.5 g of potassium carbonate were heated for 2 hours at 120° to 135° C. internal temperature under a 1.2 m packed column until 70 g of ethanol had distilled out at the top, $CO_2$ being produced at the same time. After distilling out the excess diethyl carbonate under 30 mbar, 180 g of residue were obtained. This was first distilled under 6 to 10 mbar/138°–180° C., then under 0.01 mbar/125°–145° C. 97 g of crystalline product, melting point 109°–110° C., were obtained by recrystallizing the distillate from ethanol. The yield was 60% based on urea employed.

EXAMPLE 2

N-Phenyl-N'-vinylethyleneurea 357 g (3 mol) of phenyl isocyanate were reacted, at 18° to 20° C., with 315 g (3 mol) of diethanolamine and 1,000 g of diethyl carbonate within 1 hour. After 1 hour, a further 1,832 g of diethyl carbonate (a total of 24 mol) were added and, after addition of 1.5 g of potassium carbonate, the mixture was heated for 6 hours at 120° to 130° C. internal temperature under a 1.2 m packed column. 365 g of ethanol were removed at the top, the ethanol being removed toward the end of the transesterification by stepwise reduction of the pressure down to 300 mbar. After distilling out the excess diethyl carbonate under 30 mbar, 906 g of residue were obtained. This was cleaved by dropwise addition to a preheated flask, at an internal temperature of 195° to 230° C., into which 1 g of potassium carbonate had been initially introduced, with stirring under oil-pump vacuum. 288 g (51% yield based on isocyanate employed) of the desired product distilled out, melting point 137°–140° C. (from ethanol).

EXAMPLE 3

N-(3,4-Dichlorophenyl)-N'-vinylethyleneurea 188 g (1 mol) of 3,4-dichlorophenyl isocyanate were reacted, at 18° to 20° C., with 105 g (1 mol) of diethanolamine in 300 g of diethyl carbonate within 1 hour. After 1 hour, a further 644 g of diethyl carbonate (a total of 8 mol) were added and, after addition of 0.8 g of potassium carbonate, the mixture was heated for 2.5 hours to 120° to 135° C. internal temperature under a 1.2 m packed column. 110 g of ethanol were removed at the top, the ethanol being removed toward the end of the transesterification by stepwise reduction of the pressure down to 300 mbar. After distilling out the excess diethyl carbonate under 30 mbar, 350 g of residue were obtained. This was cleaved as described in Example 2. 108 g (42% yield, based on isocyanate employed) of the desired product distilled out during this. Boiling point at 0.02 mbar, 170°–175° C., melting point 134°–136° C. (from ethanol).

EXAMPLE 4

N-(3,4-Dichlorophenyl)-N'-(2-ethylcarbonatoethyl)ethyleneurea 188 g (1 mol) of 3,4-dichlorophenyl isocyanate were reacted with 105 g (1 mol) of diethanolamine in diethyl carbonate and transesterified with diethyl carbonate as described in Example 3. To remove the catalyst, the excess diethyl carbonate was not removed but the solution was passed over an ion exchanger based on a sulphonated styrene/divinylbenzene copolymer, methylene chloride being used to wash. The eluate was completely evaporated in vacuo. 208 g (60% yield based on isocyanate employed) of the title compound were obtained by crystallization from ethanol, melting point 90°–92° C.

What is claimed is:

1. A N-vinyl ethyleneurea of the formula

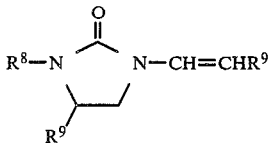

in which
R$^8$ represents a phenyl radical which is optionally monosubstituted or polysubstituted by chlorine, bromine, a nitro group, a trifluoromethyl group, an alkoxy group having 1 to 4 carbon atoms or a carbalkoxy group having 1 to 4 carbon atoms, and
R$^9$ denotes hydrogen or methyl.

* * * * *